US012695843B2

(12) United States Patent
Goel et al.

(10) Patent No.: US 12,695,843 B2
(45) Date of Patent: Jul. 28, 2026

(54) MAINTAINING NEIGHBORING CONTEXTUAL AWARENESS WITH ZOOM

(71) Applicant: NVIDIA Corporation, Santa Clara, CA (US)

(72) Inventors: Anisha Goel, Santa Cruz, CA (US); Nicola Christin Rieke, Munich (DE)

(73) Assignee: NVIDIA Corporation, Santa Clara, CA (US)

( * ) Notice: Subject to any disclaimer, the term of this patent is extended or adjusted under 35 U.S.C. 154(b) by 593 days.

(21) Appl. No.: 17/451,578

(22) Filed: Oct. 20, 2021

(65) Prior Publication Data

US 2023/0118522 A1     Apr. 20, 2023

(51) Int. Cl.
| | |
|---|---|
| *H04N 5/262* | (2006.01) |
| *A61B 1/00* | (2006.01) |
| *A61B 1/04* | (2006.01) |
| *G06V 10/25* | (2022.01) |
| *H04N 5/232* | (2006.01) |
| *H04N 23/69* | (2023.01) |

(52) U.S. Cl.
CPC ....... *H04N 5/2628* (2013.01); *A61B 1/00009* (2013.01); *A61B 1/0005* (2013.01); *A61B 1/044* (2022.02); *G06V 10/25* (2022.01); *H04N 23/69* (2023.01)

(58) Field of Classification Search
CPC ........ A61B 1/000095; A61B 1/000096; A61B 1/00009; A61B 1/044; A61B 1/0005; H04N 5/2628; H04N 26/69; H04N 23/69; G06V 10/25
See application file for complete search history.

(56) References Cited

U.S. PATENT DOCUMENTS

| | | | | |
|---|---|---|---|---|
| RE43,742 E | * | 10/2012 | Baar ..................... | G06F 3/0481 |
| | | | | 345/670 |
| 8,907,948 B2 | * | 12/2014 | Shoemaker ............ | G06T 15/20 |
| | | | | 345/418 |

(Continued)

FOREIGN PATENT DOCUMENTS

| | | |
|---|---|---|
| CN | 111557021 A | 8/2020 |

OTHER PUBLICATIONS

Comparison of six display modes for a multi-resolution foveated laparoscope (Year: 2019).*

(Continued)

*Primary Examiner* — Stephen S Hong
*Assistant Examiner* — Carl E Barnes, Jr.
(74) *Attorney, Agent, or Firm* — Lowenstein Sandler LLP

(57)     ABSTRACT

An area of interest within a visual output of a surgical site is identified. An area of interest within a visual output of a surgical site is identified. A zoom operation on the area of interest to generate a magnified area of interest is performed. An occluded region around the area of interest within the visual output is determined based on an amount of zoom associated with the zoom operation. The occluded region is a region of the visual output that becomes occluded by placing a magnified area of interest over the area of interest within the visual output. A non-linear compression to the occluded region of the visual output to generate a compressed occluded region is applied. The magnified area of interest to include the compressed occluded region is updated.

20 Claims, 8 Drawing Sheets

200

(56)         References Cited

U.S. PATENT DOCUMENTS

| 2002/0122038 A1* | 9/2002 | Cowperthwaite ....... G06T 19/20 |
| | | 345/428 |
| 2003/0052900 A1* | 3/2003 | Card ........................ G09G 5/00 |
| | | 345/660 |
| 2006/0252530 A1* | 11/2006 | Oberberger ......... G07F 17/3239 |
| | | 463/29 |
| 2007/0172112 A1* | 7/2007 | Paley .................... G06T 1/0007 |
| | | 382/128 |
| 2008/0163749 A1* | 7/2008 | Reimer ............... F41C 33/0254 |
| | | 42/122 |
| 2011/0298952 A1* | 12/2011 | Yano ..................... G06T 3/4053 |
| | | 348/E5.051 |
| 2014/0136939 A1* | 5/2014 | Chan ....................... G06F 40/18 |
| | | 715/227 |
| 2014/0189556 A1* | 7/2014 | Soo ........................ G06F 3/016 |
| | | 715/765 |
| 2015/0173846 A1* | 6/2015 | Schneider .......... A61B 1/00042 |
| | | 600/424 |
| 2018/0218482 A1* | 8/2018 | Ganesan .......... A61B 1/000095 |
| 2018/0325601 A1* | 11/2018 | Mak ..................... A61B 5/0042 |

OTHER PUBLICATIONS

Office Action for Chinese Patent Application No. 202210827159.5, mailed Jun. 20, 2025, 21 Pages.

\* cited by examiner

100

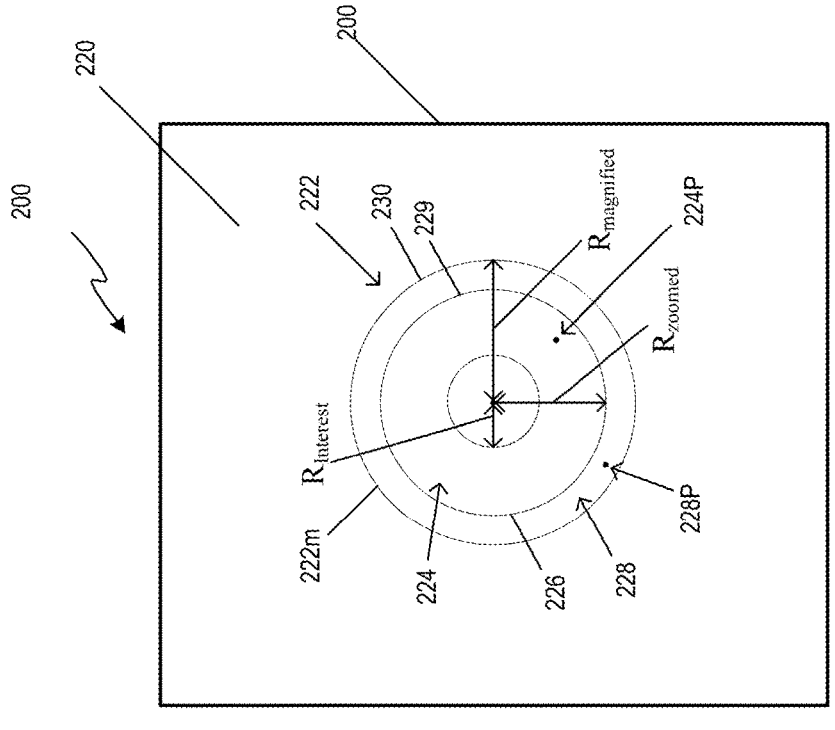
FIG. 2B
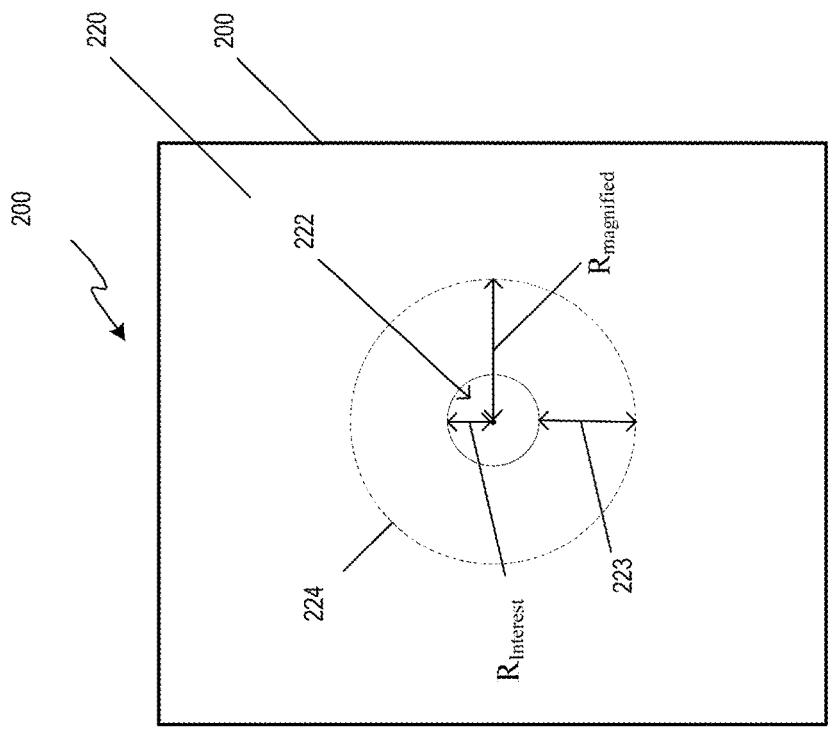
FIG. 2A

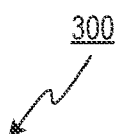

300

| Identify an area of interest within a visual output of a surgical site. 310 |
| --- |

| Perform a zoom operation on the area of interest to generate a magnified area of interest. 320 |
| --- |

| Determine, based on an amount of zoom associated with the zoom operation, an occluded region around the area of interest within the visual output, wherein the occluded region is a region of the visual output that becomes occluded by placing a magnified area of interest over the area of interest within the visual output. 330 |
| --- |

| Apply a non-linear compression to the occluded region of the visual output to generate a compressed occluded region. 340 |
| --- |

| Update the magnified area of interest to include the compressed occluded region. 350 |
| --- |

FIG. 3

MAINTAINING NEIGHBORING CONTEXTUAL AWARENESS WITH ZOOM

TECHNICAL FIELD

At least one embodiment pertains to performing zoom operations on portions of image data while maintaining contextual awareness of the zoomed in portions according to various novel techniques described herein. For example, embodiments provide contextual awareness of the area surrounding a zoomed area of interest according to various novel techniques described herein.

BACKGROUND

Endoscopes are widely used for medical procedures inside the human body. In particular, optical zoom endoscopes are used to provide high resolution imaging with close-up (e.g., zoomed-in) views of a region of interest of a wide-field view of the inside of a human body. The zoomed or magnified region of interest enable users to observe magnified images for further inspection while maintaining high image quality. Generally, to maintain context of the zoomed region of interest in view of the rest of inside the human body, the zoomed region of interest is overlaid on the wide-field view of the human body. However, the zoom region of interest occupies additional space in the wide-field view of the inside of the human body, resulting in a portion of the wide-field view of the inside of the human body being occluded by the overlaid zoomed-in region of interest. As a result, the user is unaware of details in the portion of the wide-field view of the inside of the human body being occluded by the overlaid zoomed-in region of interest. Such details may be important details for a surgeon to know during surgery.

BRIEF DESCRIPTION OF DRAWINGS

FIGS. 2A and 2B is an example of a non-linear compression performed on a portion of the frame to maintain neighboring contextual awareness during zoomed in surgical procedures, in accordance with at least one embodiment;

FIG. 3 is a flow diagram of a process of maintaining neighboring contextual awareness during zoomed in surgical procedures, in accordance with at least one embodiment;

DETAILED DESCRIPTION

Figure 1:
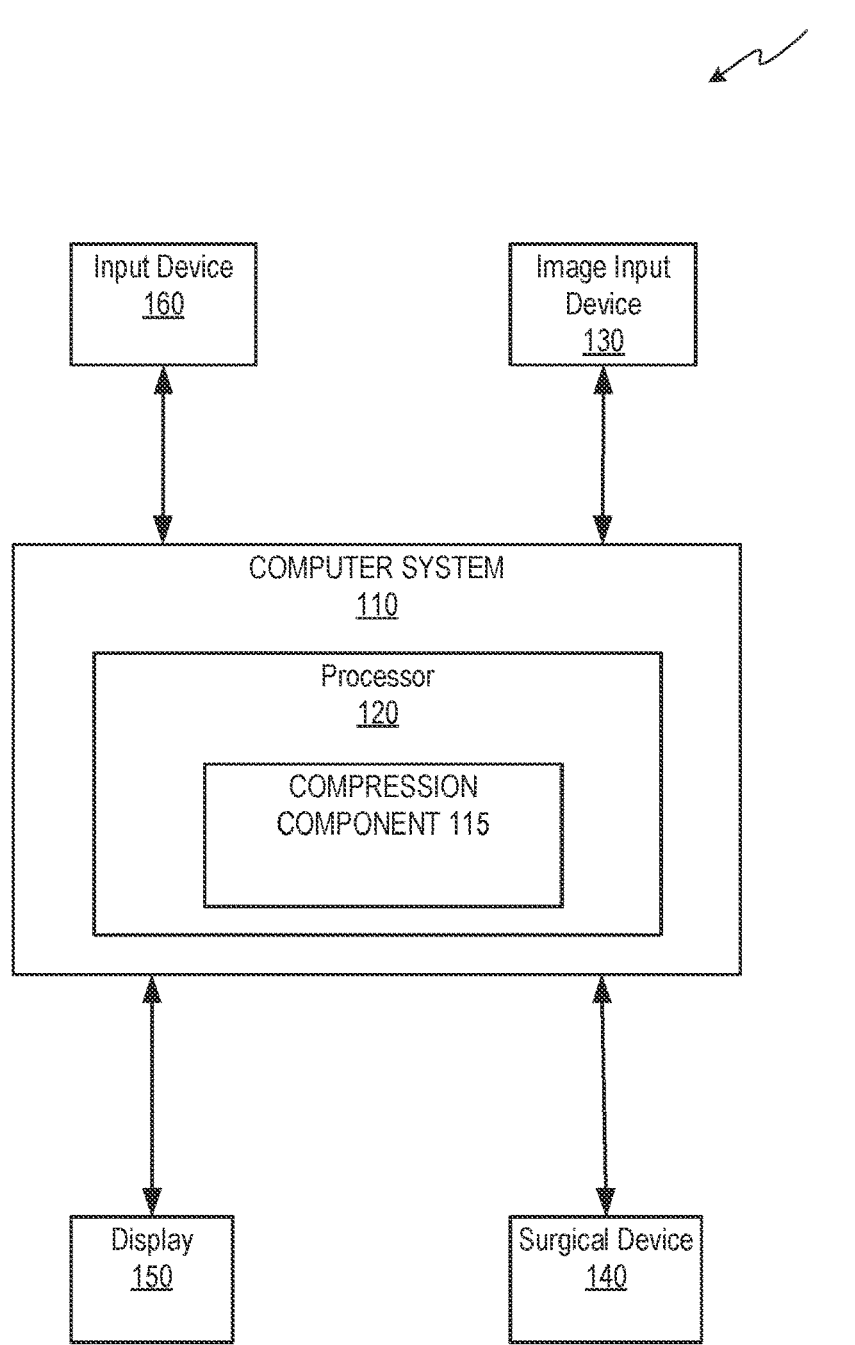
FIG. 1 is a diagram of a system for maintaining neighboring contextual awareness during zoomed in surgical procedures, in accordance with at least one embodiment.

Embodiments described herein relate to systems and methods for magnifying portions of images while maintaining neighboring contextual awareness of non-magnified portions of the images. In embodiments, an endoscope may capture images (e.g., frames of a video) of a surgical site within a body during a medical procedure. The images/video may be displayed (e.g., via a visual output) on a display viewable by a doctor during surgery or another medical operation. In some embodiments, the visual output may be a single image or a video (e.g., a sequence of image frames) of the surgical site. Depending on the embodiment, a clinician may identify an area of interest (AOI) within the visual output to focus on. Alternatively, processing logic may automatically identify the AOI. Once the area of interest within the visual output is identified, a zoom operation may be performed on the identified area of interest within the visual output.

Depending on the embodiment, the identified area of interest may be cropped from the visual output prior to performing a zoom operation on the identified area of interest. In some embodiments, a cut-off percentage is set based on a portion of the identified area of interest the clinician intends to remain zoomed in (e.g., the zoom region). Based on the set cut-off percentage, a compression region around the area of interest is determined (e.g., the remaining portion of the identified area of interest). Once the compression region is determined, non-linear compression is applied to the compression region to generate a compressed region. The compressed region may be a ring around the zoom region. In some embodiments, performing the non-linear compression of the compression region may include obtaining a scale factor based on the zoom operation and a radius of the zoom region based on the set cut-off percentage. Once the scale factor and the radius of the zoom region are obtained, a power coefficient may be determined based on the obtained scale factor and radius of the zoom region. Additionally, for each pixel located within the compression region, a power coefficient may be applied to the pixel to obtain a new pixel value to update the pixel. In some embodiments, pixel coordinates are converted from Cartesian coordinates into polar coordinates in order to apply the power coefficient to the radial coordinate of the pixel. Coordinates of pixels may then be converted back to Cartesian coordinates to obtain the new pixel values. Once the power coefficient is applied to each pixel located within the compression region, the compressed region is generated.

After generating the compressed region, the visual output is updated to include the modified area of interest, which includes the zoom region and the compressed region. Depending on the embodiment, the visual output may be updated by stitching the modified area of interest including the zoom region and the compressed region to the visual output from which the area of interest was cropped. The updated visual output including the identified area of interest having the zoom region and the compressed region may be displayed on the display device.

Aspects of the present disclosure address the above and other deficiencies by compressing portions of the surgical site occluded by the zoomed-in region of the surgical site to clinician. Additionally, and/or alternatively, the portions of the surgical site surrounding the zoomed-in region not occluded may be compressed to accommodate the increased size of the zoomed-in region.

Advantages of the present disclosure include, but are not limited to, providing contextual awareness to portions of the surgical site occluded by the zoomed-in region and portions of the surgical site surrounding the zoomed-in region, thereby, allowing the clinician to view aspects of the surgical site outside the area of interest in the zoomed-in region without being impeded.

Embodiments are discussed herein with reference to performing operations on medical images generated by endoscopes. However, it should be understood that the embodiments described herein with regards to images from endoscopes also apply to other types of medical images, which may or may not be optical images. Examples of other types of medical images to which embodiment may apply include fluoroscopy images, radiography images (e.g., x-ray images), magnetic resonance imaging (MRI) images, ultrasound images, elastography images, photoacoustic images, and so on. Additionally, embodiments described herein with regards to images from endoscopes apply to non-medical images, such as images generated for quality control purposes, artistic purposes, and so on.

FIG. 1 illustrates a system for performing zoom operations on an AOI within an image or video while maintaining neighboring contextual awareness of a surrounding region around the AOI in accordance with some embodiments of the present disclosure, shown generally as system 100. System 100 includes a computer system 110, an image input device 130, a surgical device 140, a display 150, and an input device 160. In some embodiments, one more components, such as surgical device 140, may be omitted.

The computer system 110 may be a server, a system on a chip (SoC), a desktop computer, a laptop computer, a mobile computing device, a video game console, a cloud computing environment, and/or any other computer system. In embodiments, the computer system 110 may be a component of a device such as a video game console, a mobile phone, an autonomous vehicle, a non-autonomous vehicle, a video surveillance system, a laptop computer, a desktop computer, a quality analysis (QA) inspection system, or other system. In at least one embodiment, computer system 110 may include, without limitation, one or more processors 120 representing one or a plurality of graphical processing units (GPU)s, central processing units (CPU)s, and/or any other processors. Computer system 110 may further include cache(s), data store(s), and/or other components and features not illustrated.

In at least one embodiment, computer system 110 may include data store(s) (e.g., memory). In at least one embodiment, data store(s) may be or include on-chip memory of computer system 110, which may store instructions for a compression component 115 that may execute on processor(s) 120 of computer system 110. The data stores may additionally or alternatively store one or more components of an image or moving image (e.g., video) captured by the image input device 130. In at least one embodiment, data store(s) may comprise level three ("L3") cache and/or a level two ("L2") cache that is available to processor 120 of computer system 110. Data stores may additionally or alternatively include hard disk drives and/or solid state drives.

The image input device 130 may be a device that includes one or more image sensor capable of generating image data such as images and/or video. In one embodiment, image input device 130 is an endoscope that captures images and/or video (e.g., moving images) of a surgical site. The endoscope may be inserted into a human body or animal body during surgery, and may perform surgical operations as well as generate image data of the surgical operation. Other types of medical image input devices include an ultrasound machine, an x-ray imager, an MRI machine, and so on. The image input device 130 may also be a camera (e.g., a camera of a mobile phone, a camera of a quality analysis (QA) system, or other type of image input device 130. The generated image data may include two-dimensional (2D) or three-dimensional (3D) images. The generated image data may include color images, monochrome images, images generated using a specific wavelength of light (e.g., infrared or near-infrared (NIRI) images), and/or other types of image data.

In at least one embodiment, processor(s) 120 may further include an always-on processor engine that may provide necessary hardware features to support low power sensor management and wake use cases. In at least one embodiment, an always-on processor engine may include, without limitation, a processor core, a tightly coupled RAM, supporting peripherals (e.g., timers and interrupt controllers), various I/O controller peripherals, and routing logic.

In at least one embodiment, processor(s) 120 may further include a real-time camera engine that may include, without limitation, a dedicated processor subsystem for handling real-time camera management. In at least one embodiment, processor(s) 120 may further include a signal processor such as a high-dynamic range signal processor that may include, without limitation, an image signal processor. Processor(s) 120 may further interact with a camera (e.g., image capture device 130) or image sensor for receiving and processing received images.

The processor 120 such as the GPU can generate a feed of frames (e.g., output images) to a display device (e.g., display 150) operably coupled to the computer system 110. In some embodiments, the GPU can include multiple cores, and each core is capable of executing multiple threads. Each core may run multiple threads concurrently (e.g., in parallel).

In at least one embodiment, a surgical device 140 performs, based on control by a clinician, surgical procedures within the surgical site. In some embodiments, the surgical device 140 may be coupled to the computer system 110. In at least one embodiment, the surgical device 140 may include, without limitation, one or more cutting instruments (e.g., scissors, surgical blades, knives, and scalpels), grasping instruments (e.g., forceps), retractors, and/or any other surgical instruments. In at least one embodiment, computer system 110 may include input device 160 that provides the clinician with the ability to manipulate a display of the still images and/or moving images of the surgical site captured by the image input device 130.

In some embodiments, the computer system 110 includes a compression component 115 executed by one or more processors 120. Compression component 115 may be implemented using one or more processors 120, and optionally one or more other components. The compression component 115 can identify an AOI (e.g., of an area of the surgical site) within received image data and magnify the AOI while maintaining neighboring contextual awareness around the AOI by performing non-linear compression on a portion of the zoomed or magnified AOI (e.g., area of the surgical site).

In at least one embodiment, the compression component 115 identifies an area of interest in a visual output of a surgical site. In some embodiments, the area of interest in the visual output of the surgical site may be selected in real-time by a clinician. Depending on the embodiment, the area of interest may be identified, by image processing, based on one of: the presence of a surgical instrument, bleeding of detected in the surgical site, a specific anatomy located within the surgical site, or any other suitable identifier obtainable by image processing. The image processing is trained by machine learning models to assist with further detection of area of interest within the surgical site. Once the area of interest is detected, the machine learning model outputs coordinates of the area of interest (e.g., coordinates of the center of the area of interest and/or the radius of the area of interest.) Additionally and/or alternatively, during play back (e.g., non-live surgical procedures) the clinician may identify an area of interest by moving a mouse pointer over the area of interest the clinician wishes to designate as the area of interest. Accordingly, the mouse pointer would be designated as the center of the area of interest. The compression component 115 magnifies the area of interest. Depending on the embodiment, the clinician may identify a magnification value to apply to the area of interest. In other embodiments, the area of interest may be magnified by a predetermined magnification value. The compression component 115 can determine a portion of the magnified area of interest to compress based on a cut-off coefficient (e.g., compression region). In some embodiments, the cut-off coefficient is determined based on a radius of a portion of the magnified area of interest the clinician intends to remain magnified without compression selected between an original radius of the area of interest prior to magnification and the radius of the magnified area of interest. Accordingly, the cut-off coefficient is used to identify the compression region within the magnified area of interest in order to determine values of the pixel within the compression region prior to magnification to compress. Additionally, or alternatively, an occluded region of the image may be compressed using a non-linear compression and included in the compression region. According to the non-linear compression, an amount of compression may be inversely proportional to a distance from a center of the area of interest. In at least one embodiment, the compression component 115 can apply non-linear compression to the occluded region of the image (e.g., which may be a difference between the size of the magnified AOI and the non-magnified AOI, and a result may be included in the compression region of the magnified area of interest. After compression of the compression region, the compression component 115 may stitch the magnified area of interest including the compressed compression region to the visual output at a location of the original area of interest in the visual output.

FIGS. 2A and 2B illustrate a non-linear compression performed on a portion of a frame or image to maintain neighboring contextual awareness during zooming in accordance with at least one embodiment. The non-linear compression may be performed in real time or near-real time during surgery for example, so that a doctor views current frames of a video (indicating what is currently viewed, for example, by an endoscope) with zoomed in AOIs. The non-linear compression may also be performed on previously generated videos and/or images to generate zoomed-in AOIs on such videos and/or images. Depending on the embodiment, image 200 may be a visual output (e.g., image or frame of a video) showing a surgical site 220.

Referring to FIG. 2A, the compression component 115 of computer system 110 may identify an area of interest 222 in the image 200 (e.g., in surgical site 220 shown in the image 200), as described above. Upon determining the area of interest 222 in the image 200, the compression component 115 may perform a zoom operation to magnify the area of interest 222 by a configurable zoom factor (e.g., $Z_{factor}$) (e.g., 2×, 4×, 6×, 8×, etc.) to a magnified area of interest 224 having a magnified radius (e.g., $R_{magnified}$).

In one embodiment, the magnified radius $R_{magnified}$ is equivalent to half of the zoom factor $Z_{factor}$ multiplied by a radius of the area of interest (e.g., $R_{interest}$). Half of the zoom factor $Z_{factor}$ (e.g., 1×, 2×, 3×, 4×, etc.) represents a scale factor (e.g., s) in a single direction. The calculation of the magnified radius $R_{magnified}$ may be as follows:

$$R_{magnified}=s*R_{interest} \qquad (1)$$

6

Accordingly, to determine a radius of the area of interest $R_{Interest}$ in the image 200 of the surgical site 220, the magnified radius $R_{magnified}$ may be divided by the scale factor s. The calculation of the radius of the area of interest $R_{interest}$ is as follows:

$$R_{interest}=R_{magnified}/s \qquad (2)$$

In embodiments, an occluded portion 223 of the image 200 may be a difference between the initial area of interest 222 and the magnified area of interest 224.

In some embodiments, referring to FIG. 2B, the compression component 115 sets a cut-off coefficient. The cut-off coefficient represents a percentage of the magnified area of interest 222 m (e.g., 85% or 0.85) that the user wishes to maintain zoomed in and uncompressed (e.g., the zoomed zone 224). Accordingly, the remaining portion of the magnified area of interest (e.g., a compression zone 228) is to be compressed.

Once the cut-off coefficient is set, the compression component 115 determines a radius of the zoomed zone (e.g., $R_{zoomed}$). The cut-off coefficient is equivalent to the radius of the zoomed zone $R_{zoomed}$ divided by the magnified radius $R_{magnified}$. The calculation of the cut-off coefficient is as follows:

$$\text{cut-off coefficient}=R_{Zoomed}/R_{magnified} \qquad (3)$$

Accordingly, to determine the radius of the zoomed zone $R_{zoomed}$, the compression component 115 multiplies the cut-off coefficient by the magnified radius $R_{magnified}$. Once the radius of the zoomed zone $R_{zoomed}$ is determined, the area between a circle 226 generated by the zoomed zone $R_{zoomed}$ and the circle generated by the radius $R_{magnified}$ (e.g., the magnified area of interest 222 m) is the compression zone 228. Subsequently, the area between a center of the magnified area of interest 222 m and the circle generated by the zoomed zone $R_{zoomed}$ (e.g., circle 226) is the zoomed zone 224. The calculation of the radius of the zoomed zone $R_{zoomed}$ is as follows:

$$R_{Zoomed}=\text{cut-off coefficient}\times R_{magnified} \qquad (4)$$

In embodiments, the occluded region 223 and/or a portion of the AOI 222 is compressed into the compression zone 228 according to a non-linear compression. An inner-most diameter 229 of the compression zone 228 may have a same magnification as the zoomed zone 224. An outer-most diameter 230 of the compression zone 228 may have a same magnification as a remainder of the image 200. Thus, the inner-most diameter 230 of the compression zone 228 may stitch successfully to zoomed zone 224, and the outer-most diameter 230 of the compression zone 228 may stitch successfully to a remainder of image 200.

Once the radius of the zoomed zone $R_{zoomed}$ is determined, the compression component 115 may determine a power coefficient of a power law to apply to compression of a pixel within the compression zone 228. The power law equation may be the scale factor s multiplied by the radius of the zoomed zone $R_{zoomed}$ raised to the power coefficient P. The calculation of the power coefficient P is as follows:

$$R_{zoomed}=s*R_{Zoomed}^{P} \qquad (5)$$

The calculation of the power coefficient P can be simplified to:

$$\text{power coefficient}P=(\log R_{zoomed}-\log s)/\log R_{zoomed} \qquad (6)$$

or $$\text{power coefficient}P=1-(\log s/\log R_{zoomed}). \qquad (7)$$

The compression component 115 may determine whether to apply compression to a pixel based on a compression threshold. In one embodiment, the compression threshold is satisfied if a radius of the pixel ($R_{pixel}$, a distance from the pixel to the center of the magnified area of interest 222 m) squared is greater than the radius of the zoomed zone $R_{zoomed}$ squared. The radius of the pixel $R_{pixel}$ squared is equivalent the x coordinate of the pixel (e.g., $x_{pixel}$) squared plus they coordinate of the pixel (e.g., $y_{pixel}$) squared with respect to the center of the magnified area of interest 222 m. The center of the magnified area of interest 222 m may be determined by a dimension of the magnified area of interest 222 m (e.g., $D_{magnified}$) divided by 2. Accordingly, the radius of the pixel $R_{pixel}$ squared is equivalent the x coordinate of the pixel $x_{pixel}$ minus half of the dimension of the magnified area $D_{magnified}$ squared plus the y coordinate of the pixel $y_{pixel}$ minus half of the dimension of the magnified area $D_{magnified}$ squared. The calculation of the radius of the pixel $R_{pixel}$ squared is as follows:

$$R_{pixel}^2=(x_{pixel}-(D_{magnified}/2))^2+(y_{pixel}-(D_{magnified}/2))^2 \tag{8}$$

or $$R_{pixel}^2=\tfrac{1}{4}[(2*x_{pixel}-D_{magnified})^2-(2*y_{pixel}-D_{magnified})] \tag{9}$$

The radius of the zoomed zone $R_{zoomed}$ squared is equivalent to the center of the magnified area of interest 222 m squared multiplied by the cut-off coefficient squared. As previously noted, the center of the magnified area of interest 222 m is determined by a dimension of the magnified area of interest 222 m (e.g., $D_{magnified}$) divided by 2. Accordingly, radius of the zoomed zone $R_{zoomed}$ squared is equivalent to half of the dimension of the magnified area $D_{magnified}$ squared multiplied by the cut-off coefficient squared. The calculation of the radius of the zoomed zone $R_{zoomed}$ squared is as follows:

$$R_{zoomed}^2=((D_{magnified}/2)*\text{cut-off coefficient})^2 \tag{10}$$

or $$R_{zoomed}^2=(D_{magnified}/2)^{2}*\text{cut-off coefficient}^2 \tag{11}$$

or $$R_{zoomed}^2=(D_{magnified}^2/4)*\text{cut-off coefficient}^2 \tag{12}$$

Accordingly, the compression threshold may be computed as follows:

$$\tfrac{1}{4}[(2*x_{pixel}-D_{magnified})^2-(2*y_{pixel}-D_{magnified})]^2 > (D_{magnified}^2/4)*\text{cut-off coefficient}^2 \tag{13}$$

The compression component 115, based on determining that a pixel (e.g., pixel 224P) does not satisfy the compression threshold, does not compress or modify the pixel (e.g., pixel 224P). The compression component 115, based on determining that a pixel satisfies the compression threshold, applies non-linear compression to the pixel (e.g., pixel 228P). In one embodiment, non-linear compression is applied to pixels in occluded region 223. In one embodiment, to apply non-linear compression to a pixel in occluded region 223, compression component 115 determines polar coordinates for the pixel, applies a power coefficient P to the radial coordinates to determine new polar coordinates for the pixel, and converts the new polar coordinates back to Cartesian coordinates.

In one embodiment, to apply non-linear compression to a pixel 228P (e.g., that is in compression region 228), the compression component 115 determines coordinates of the pixel 228P with respect to the center of the magnified area of interest 222 m (e.g., $x_{cor}$, $y_{cor}$ coordinates) by subtracting the $x_{pixel}$ and $y_{pixel}$ coordinates from the coordinates of the center of the magnified area of interest 222 m. As previously noted, the center of the magnified area of interest 222 m is determined by a dimension of the magnified area of interest 222 m (e.g., $D_{magnified}$) divided by 2. Accordingly, the calculation for $x_{cor}$, $y_{cor}$ coordinates is as follows:

$$x_{cor}=x_{pixel}-(D_{magnified}/2); \tag{14}$$

and $$y_{cor}=y_{pixel}-(D_{magnified}/2) \tag{15}$$

Once the coordinates of the pixel 228P are determined, the compression component 115 determines the coordinates of the pixel 228P in the visual output prior to magnification (e.g., $x_{prior}$, $y_{prior}$ coordinates). To determine $x_{prior}$, $y_{prior}$ coordinates, the compression component 115 divides each of $x_{cor}$, $y_{cor}$ coordinates by the scale factor s. Accordingly, the calculation for $x_{prior}$, $y_{prior}$ coordinates is as follows:

$$x_{prior}=x_{cor}/s \tag{16}$$

and $$y_{prior}=y_{cor}/s. \tag{17}$$

Once the $x_{prior}$, $y_{prior}$ coordinates of the pixel 228P in the visual output prior to magnification are determined, the compression component 115 obtains the polar coordinates of $x_{prior}$, $y_{prior}$ coordinates (e.g., radial coordinate $\varrho$, angular coordinate $\theta$). Depending on the embodiment, the polar coordinates may be obtained by a get polar coordinate function or any other suitable function. As a result, the polar coordinates associated with the Cartesian coordinates ($x_{prior}$, $y_{prior}$) are returned for the pixel 228P in the visual output prior to magnification (e.g., the old radial coordinate $\varrho_{old}$) and the angular coordinates of pixel 228P in the visual output prior to magnification (e.g., $\theta$). Depending on the embodiment, due to the visual output being magnified, the visual output is not manipulated enough to change the angular coordinate between the visual output prior to magnification and the angular coordinate after magnification.

Once the polar coordinates are returned, the compression component 115 may apply the power coefficient P to the old radial coordinate $\varrho_{old}$ to obtain a new polar coordinate (e.g., $\varrho_{new}$). To apply the power coefficient P to the old radial coordinate $\varrho_{old}$, the compression component 115 raises the old radial coordinate $\varrho_{old}$ to the power coefficient P. Accordingly, the calculation for the new polar coordinate $\varrho_{new}$ is as follows:

$$\varrho_{new}=\varrho_{old}^{P} \tag{18}$$

Once the new polar coordinate $\varrho_{new}$ is determined, the compression component 115 determines coordinates to replace the $x_{pixel}$ and $y_{pixel}$ coordinates of pixel 228P by obtaining the Cartesian coordinates of $\varrho_{new}$, $\theta$. Depending on the embodiment, the Cartesian coordinates may be obtained by a get Cartesian coordinate function or any other suitable function. As a result, the Cartesian coordinates ($x_{new}$, $y_{new}$) associated with the radial coordinates ($\varrho_{new}$, $\theta$) are returned. Accordingly, the compression component 115 may replace the coordinate ($x_{pixel}$, $y_{pixel}$) with a pixel value at coordinates ($x_{new}$, $y_{new}$) from the visual output prior to the magnification.

In some embodiments, the shape used to zoom into the area of interest or designate the various portions of the magnified area of interest may be any shape other than a circle that is suitable to designate a zoomed area (e.g., rectangle, oval, square, etc.). Accordingly, the calculations may be adjusted to accommodate the different shapes applied to the zoomed area of interest or various portions of the magnified area of interest. Additionally, and/or alternatively, any combinations of shapes may be applied (e.g., a square shape for the magnified area of interest 222 m, a circular shape for the zoomed region 224, and a square shape for the compression region 228).

FIG. 3 depicts a flow diagram of an example method 300 for maintaining neighboring contextual awareness with zoom, in accordance with one or more aspects of the present disclosure. The method may be performed by processing logic that may comprise hardware (circuitry, dedicated logic, etc.), computer readable instructions (run on a general purpose computer system or a dedicated machine), or a combination of both. In an illustrative example, method 300 may be performed by a processor, such as processor 120 (e.g., GPU) in FIG. 1. Alternatively, some or all of method 300 might be performed by another module or machine. It should be noted that blocks depicted in FIG. 3 could be performed simultaneously or in a different order than that depicted.

At block 310, the processing logic identifies an area of interest within a visual output (e.g., image or video) of an imaging device. In one embodiment, the visual output depicts a surgical site. The area of interest may be determined manually based on user input (e.g., based on coordinates of a mouse pointer) and/or automatically based on image processing and/or application of machine learning. Depending on the embodiment, after identification of the area of interest within the visual output, the processing logic crops the area of interest from the visual output. In one embodiment, processing logic determines a size that the area of interest will have after magnification, and crops a size equal to the magnified size of the area of interest.

At block 320, the processing logic performs a zoom operation on the area of interest to generate a magnified area of interest, as discussed herein above.

At block 330, the processing logic sets, based on a portion of the magnified area of interest to maintain, a cut-off percentage. The portion of the magnified area of interest to maintain may be a zoom region. As described previously, the cut-off percentage (e.g., cut-off coefficient) represents a percentage of the magnified area of interest that the user wishes to maintain zoomed in and uncompressed (e.g., 85%, 80%, 75%, 70%, and so on). The remaining portion of the magnified area of interest may be compressed by the processing logic. In one embodiment, processing logic determines an occluded region that will be occluded by the magnified area of interest.

At block 340, the processing logic determines, based on the cut-off percentage, a compression region around the area of interest within the visual output. As described previously, the compression region around the area of interest within the visual output is an area between a circle generated by a radius determined by the cut-off percentage and a circle generated by a radius determined by the magnified area of interest. In one embodiment, processing logic compresses the occluded region.

In one embodiment, the processing logic applies a non-linear compression to compress data (e.g., the data from the occluded region) into the compression region of the visual output. In one embodiment, to apply the non-linear compression to the region, the processing logic obtains, based on the zoom operation, a scale factor and a radius of the zoom region, based on the cut-off percentage. As described previously, the processing logic determines a power coefficient based on the scale factor and the radius of the zoom region.

Once the power coefficient is determined, the processing logic applies the power coefficient to each pixel within the compression region to obtain a new pixel value for the respective pixel in the compression zone. As described previously, to obtain the new pixel value for the respective pixel in the compression zone, the processing logic obtains polar coordinates of the respective pixel in the compression zone (or occluded region) and applies the power coefficient to the radial coordinate of the respective pixel in the compression zone (or occluded region) by raising the radial coordinate to the power coefficient. Once the radial coordinate is raised to the power coefficient, the processing logic obtains a Cartesian coordinate of the radial coordinate raised to the power coefficient and the angular coordinate of the respective pixel in the compression zone.

Once the new pixel value is obtained, the processing logic replaces the respective pixel in the compression zone with the new pixel value (e.g., from the occluded region) and at block 350, the processing logic updates the magnified area of interest to include the compressed region.

In some embodiments, the processing logic outputs a live feed of a video comprising the visual output and the magnified area of interest. To output the live feed of the video comprising the visual output and the magnified area of interest, the processing logic may overlay the magnified AOI (including the compression region) over the visual output. This may include stitching the magnified area of interest comprising the compressed region to the visual output.

In some embodiments, the visual output may be a frame of a video of a surgical site. Accordingly, the processing logic may identify an area of interest within each frame of video of the surgical site, perform a zoom operation on the area of interest to generate a magnified area of interest, set, based on a portion of the magnified area of interest to maintain, a cut-off percentage, determine, based on the cut-off percentage, a compression region around the area of interest within each frame of the video, apply a non-linear compression to an occluded region to generate the contents of the compression region, and update the magnified area of interest to include the compressed region.

Figure 4:
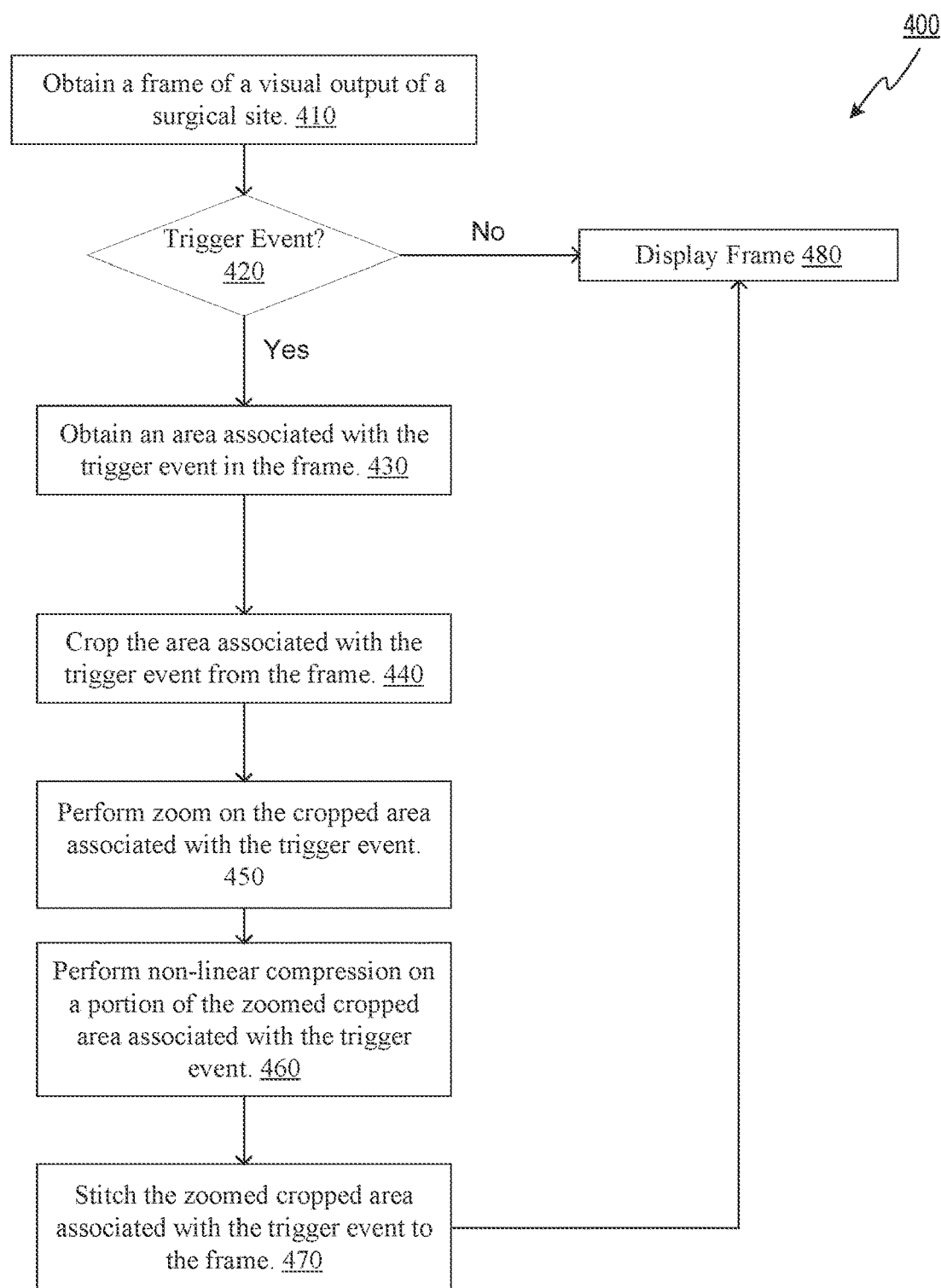
FIG. 4 is a flow diagram of a process of maintaining neighboring contextual awareness during zoomed in surgical procedures based on an event trigger, in accordance with at least one embodiment.

FIG. 4 depicts a flow diagram of an example method 400 for maintaining neighboring contextual awareness with zoom based on an event trigger, in accordance with one or more aspects of the present disclosure. The method may be performed by processing logic that may comprise hardware (circuitry, dedicated logic, etc.), computer readable instructions (run on a general purpose computer system or a dedicated machine), or a combination of both. In an illustrative example, method 400 may be performed by a processor, such as processor 120 (e.g., GPU) in FIG. 1. Alternatively, some or all of method 400 might be performed by another module or machine. It should be noted that blocks depicted in FIG. 4 could be performed simultaneously or in a different order than that depicted.

Figure 5A:
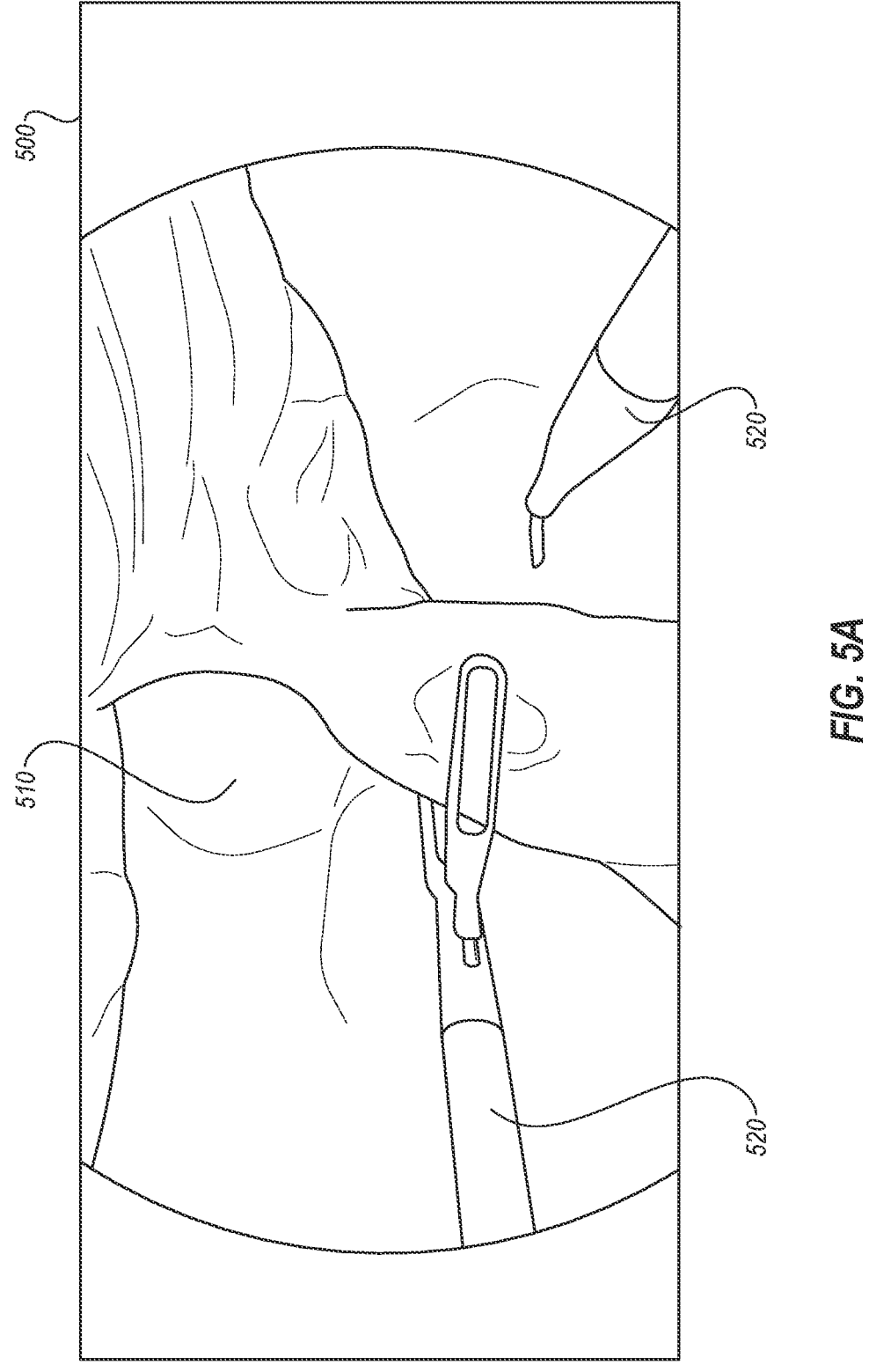
FIG. 5A-5C is an example of neighboring contextual awareness during zoomed-in surgical procedure is maintained based on an event trigger, in accordance with at least one embodiment.

At block 410, the processing logic obtains a frame of a visual output of a surgical site. Referring to FIG. 5A, the frame 500 is a visual output of surgical site 510. The frame 500 of the surgical site 510 may include tissue or any other objects found in a surgical site and a surgical instrument 520. Depending on the embodiment, the frame 500 of the visual output of the surgical site 510 may be received from an endoscope (not shown).

Figure 5B:
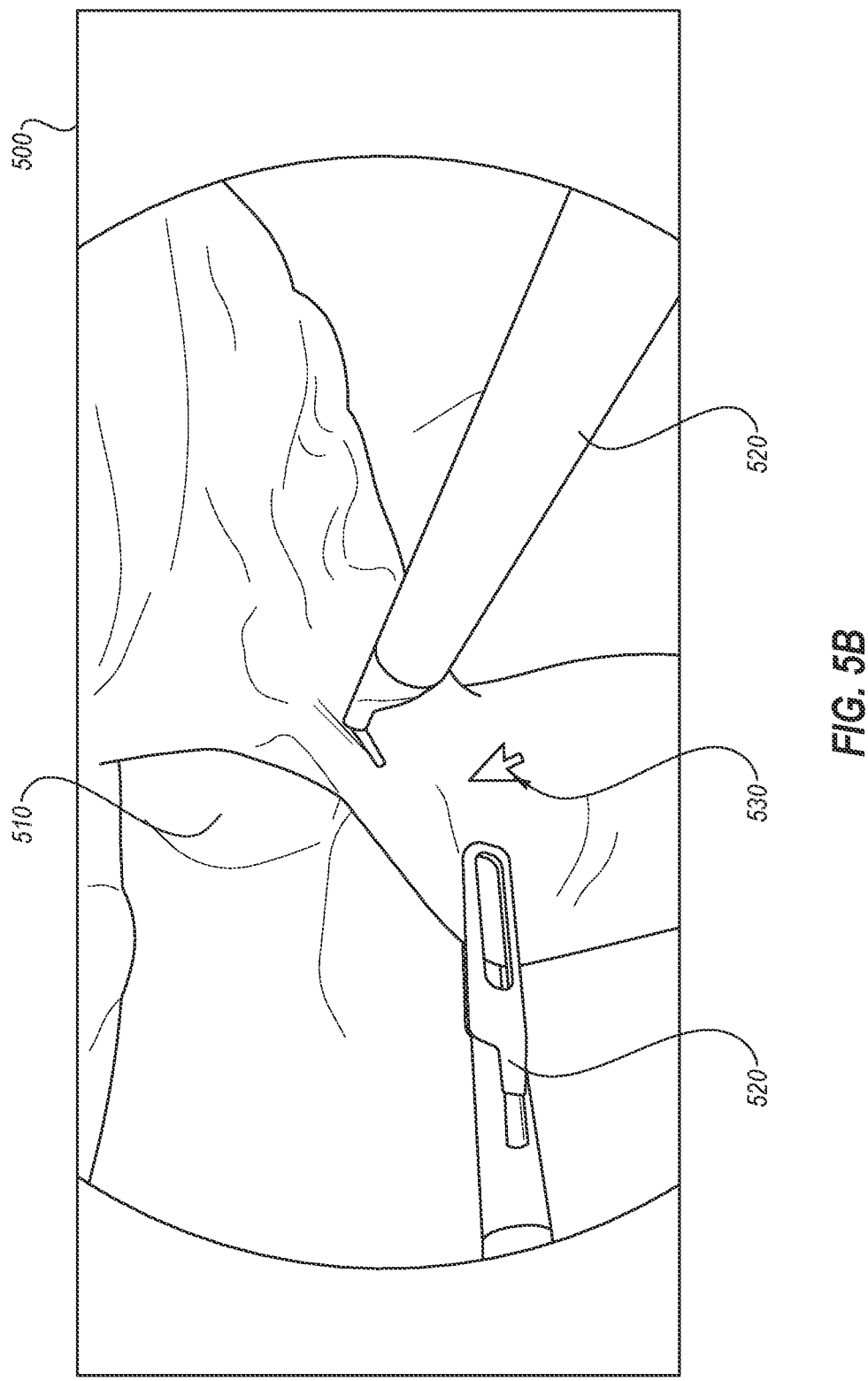

At block 420, the processing logic determines whether a trigger event has occurred. Depending on the embodiment, the trigger event may be input from a mouse click as shown by a cursor 530 in frame 500 (e.g., referring to FIG. 5B). Depending on the embodiment, the trigger event may be based on a location of the surgical instrument 520. In some embodiments, the surgical instrument is determined by a learning model that identifies equipment, instrument, and other tools in the surgical site 510. In some embodiments, based on the learning model, the processing logic can determine that a trigger event has occurred based on the manipulation of the surgical instrument. Additionally, and/or alternatively, in some embodiments, the processing logic can determine that a trigger event has occurred based on the presence of the surgical instrument 520 in the frame 500. In some embodiment, no trigger event has occurred, accordingly, the processing logic proceeds to block 480, to display the frame on a display device.

At block 430, the processing logic obtains an area associated with the trigger event in the frame of the visual output of the surgical site. Depending on the embodiment, the area associated with the trigger event in the frame may be derived based on a position of the cursor 530 (e.g., a pointer end of cursor 530 would indicate the center of the area). In some embodiments, the area associated with the trigger event in the frame may be generated based on a position of the surgical instrument 520 (e.g., a distal end of the surgical instrument 520 would indicate the center of the area). The distal end of the surgical instrument 520 may be the portion of the surgical instrument 520 furthest from a clinician. Depending on the embodiment, the area associated with the trigger event in the frame may be an area defined by a predefined distance from the position of the cursor 530 or surgical instrument 520.

At block 440, the processing logic crops an area of interest associated with the trigger event in the frame. The cropped AOI may be a circle having a predetermined radius that centers on the location of the surgical instrument or cursor, for example. The processing logic proceeds to block 450, at which processing logic performs a zoom operation on the cropped area associated with the trigger event in the frame (e.g., zoomed cropped area 540). Depending on the embodiment, the zoom operation may be controlled by manipulation of the endoscope (not shown), input devices in the surgical system (e.g., foot pedals), scroll wheel of the mouse, left and/or right click of the mouse, and any suitable means for adjusting the zoom operation to control the amount of zoom (e.g., 2×, 3×, 4×, etc.).

At block 460, the processing logic performs non-linear compression on a boundary of the zoomed cropped area 540 and/or on an occluded region that will be blocked by the zoomed cropped area 540. As described previously, to apply the non-linear compression to the portion of the zoomed cropped area 540, the processing logic may obtain, based on the zoom operation, a scale factor and a radius of the zoom cropped area, based on a cut-off percentage. The cut-off percentage may be set, by the processing logic, based on a portion of the zoomed cropped area 540 the clinician or processing logic intends to maintain uncompressed (e.g., 85% of the zoomed cropped area 540). The remaining portion of the zoomed cropped area 540 (e.g., the boundary of the zoomed cropped area 540) may be compressed, by the processing logic.

As described previously, the processing logic determines a power coefficient based on the scale factor and the radius of a zoom region determined based on the cut-off percentage. Once the power coefficient is determined, the processing logic applies the power coefficient to each pixel within the boundary of the zoomed cropped area 540 to obtain a new pixel value for the respective pixel in the boundary of the zoomed cropped area 540. In one embodiment, processing logic applies the power coefficient to each pixel in an occluded region that will be occluded by the zoomed cropped area 540. As described previously, to obtain the new pixel value for the respective pixel in the boundary of the zoomed cropped area 540, the processing logic obtains polar coordinates of the respective pixel in the boundary of the zoomed cropped area 540 and/or in the occluded region and applies the power coefficient to the radial coordinate of the respective pixel in the portion of the zoomed cropped area 540 and/or in the occluded region by raising the radial coordinate to the power coefficient. Once the radial coordinate is raised to the power coefficient, the processing logic obtains a Cartesian coordinate of the radial coordinate raised to the power coefficient and the angular coordinate of the respective pixel in the boundary of the zoomed cropped area 540. As described previously, the processing logic uses a pixel value located at the Cartesian coordinate of the radial coordinate raised to the power coefficient and the angular coordinate of the respective pixel in the boundary of the zoomed cropped area 540 to replace the respective pixel in the Cartesian coordinate of the radial coordinate raised to the power coefficient and the angular coordinate of the respective pixel in the boundary of the zoomed cropped area 540.

Figure 5C:
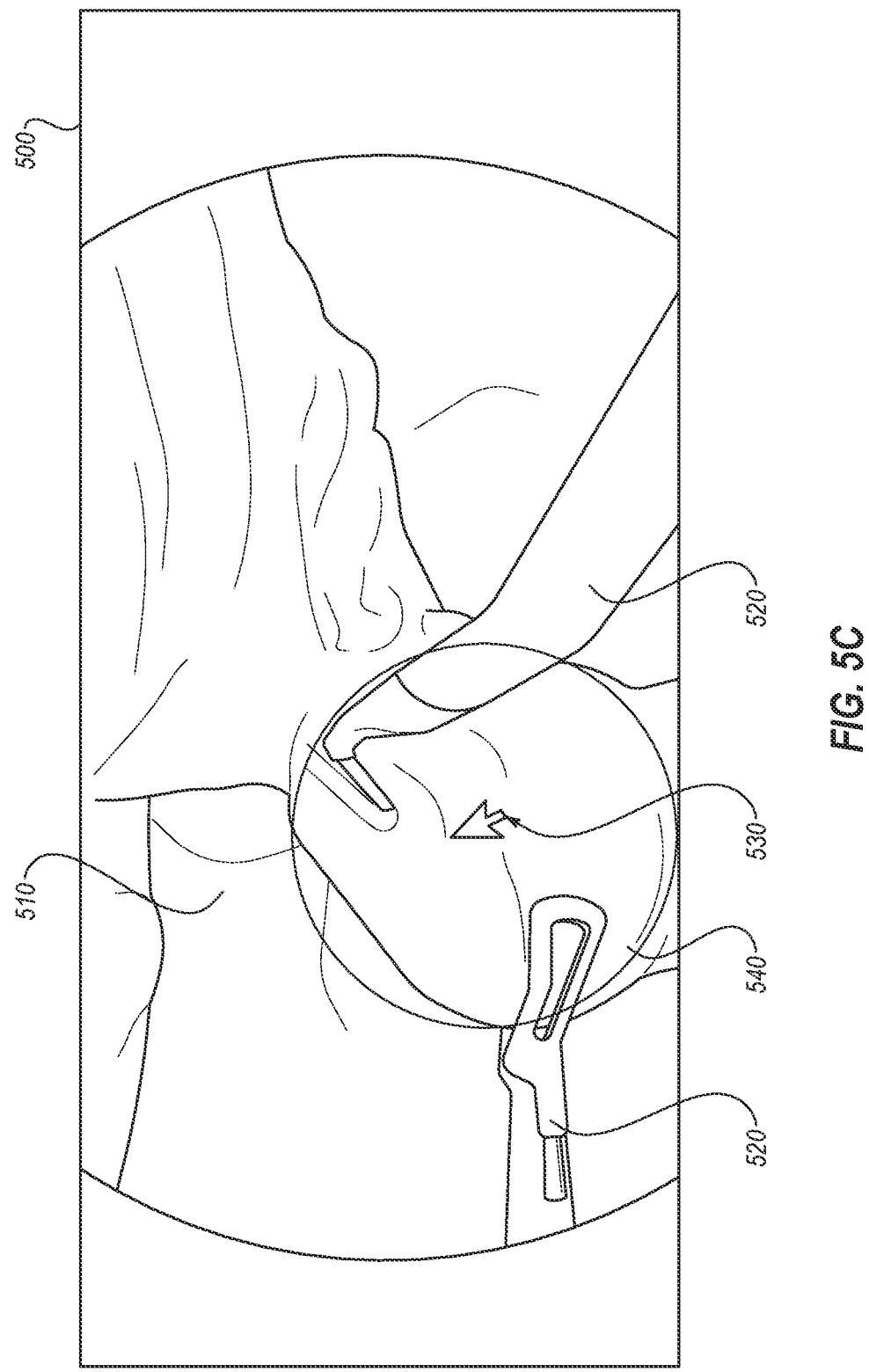

Once each pixel in the boundary of the zoomed cropped area 540 and/or in the occluded region is compressed, at block 470, the processing logic stitches the zoomed cropped area 540 to a position of the area with the trigger event in the frame. The processing logic proceeds to block 480 and displays the frame on a display device (referring to FIG. 5C). Additionally, depending on the embodiments, additional image operations may be performed on the zoomed cropped area 540 (e.g., thresholding, contrast adjustment, adding artificial exposure, edge detection, etc.).

Figure 6:
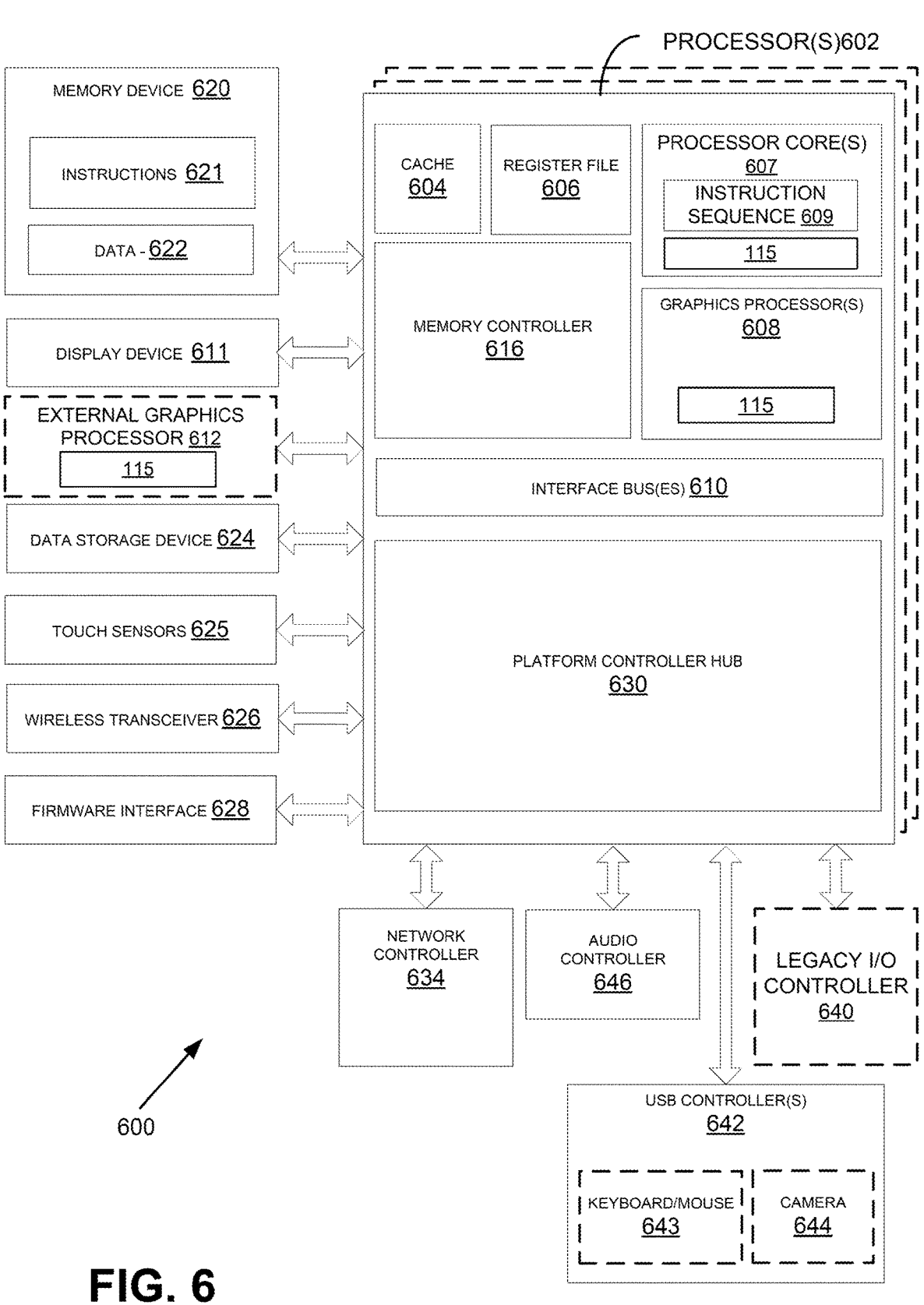
FIG. 6 is a block diagram illustrating a computer system, according to at least one embodiment.

FIG. 6 is a block diagram of a processing system 600, according to at least one embodiment. Processing system 600 may correspond to computer system 110 of FIG. 1 in embodiments. In at least one embodiment, system 600 includes one or more processors 602 and one or more graphics processors 608, and may be a single processor desktop system, a multiprocessor workstation system, or a server system having a large number of processors 602 or processor cores 607. In at least one embodiment, system 600 is a processing platform incorporated within a system-on-a-chip (SoC) integrated circuit for use in mobile, handheld, or embedded devices.

In at least one embodiment, system 600 can include, or be incorporated within, a server-based gaming platform, a game console, including a game and media console, a mobile gaming console, a handheld game console, or an online game console. In at least one embodiment, system 600 is a mobile phone, a smart phone, a tablet computing device or a mobile Internet device. In at least one embodiment, processing system 600 can also include, couple with, or be integrated within a wearable device, such as a smart watch wearable device, a smart eyewear device, an augmented reality device, or a virtual reality device. In at least one embodiment, processing system 600 is a television or set top box device having one or more processors 602 and a graphical interface generated by one or more graphics processors 608. In at least one embodiment, system 600 is a desktop computer or a server computer.

In at least one embodiment, one or more processors 602 each include one or more processor cores 607 to process instructions which, when executed, perform operations for system and user software. In at least one embodiment, each of one or more processor cores 607 is configured to process a specific instruction sequence 609. In at least one embodiment, instruction sequence 609 may facilitate Complex Instruction Set Computing (CISC), Reduced Instruction Set Computing (RISC), or computing via a Very Long Instruction Word (VLIW). In at least one embodiment, processor cores 607 may each process a different instruction sequence 609, which may include instructions to facilitate emulation of other instruction sequences. In at least one embodiment, processor core 607 may also include other processing devices, such a Digital Signal Processor (DSP).

In at least one embodiment, processor 602 includes a cache memory 604. In at least one embodiment, processor 602 can have a single internal cache or multiple levels of internal cache. In at least one embodiment, cache memory is shared among various components of processor 602. In at least one embodiment, processor 602 also uses an external cache (e.g., a Level-3 (L3) cache or Last Level Cache (LLC)) (not shown), which may be shared among processor cores 607 using known cache coherency techniques. In at least one embodiment, a register file 606 is additionally included in processor 602, which may include different types of registers for storing different types of data (e.g., integer registers, floating point registers, status registers, and an instruction pointer register). In at least one embodiment, register file 606 may include general-purpose registers or other registers.

In at least one embodiment, one or more processor(s) 602 are coupled with one or more interface bus(es) 610 to transmit communication signals such as address, data, or control signals between processor 602 and other components in system 600. In at least one embodiment, interface bus 610 can be a processor bus, such as a version of a Direct Media Interface (DMI) bus. In at least one embodiment, interface bus 610 is not limited to a DMI bus, and may include one or more Peripheral Component Interconnect buses (e.g., PCI, PCI Express), memory busses, or other types of interface busses. In at least one embodiment processor(s) 602 include an integrated memory controller 616 and a platform controller hub 630. In at least one embodiment, memory controller 616 facilitates communication between a memory device and other components of system 600, while platform controller hub (PCH) 630 provides connections to I/O devices via a local I/O bus.

In at least one embodiment, a memory device 620 can be a dynamic random access memory (DRAM) device, a static random access memory (SRAM) device, flash memory device, phase-change memory device, or some other memory device having suitable performance to serve as process memory. In at least one embodiment, memory device 620 can operate as system memory for system 600, to store data 622 and instructions 621 for use when one or more processors 602 executes an application or process. In at least one embodiment, memory controller 616 also couples with an optional external graphics processor 612, which may communicate with one or more graphics processors 608 in processors 602 to perform graphics and media operations. In at least one embodiment, a display device 611 can connect to processor(s) 602. In at least one embodiment, display device 611 can include one or more of an internal display device, as in a mobile electronic device or a laptop device, or an external display device attached via a display interface (e.g., DisplayPort, etc.). In at least one embodiment, display device 611 can include a head mounted display (HMD) such as a stereoscopic display device for use in virtual reality (VR) applications or augmented reality (AR) applications.

In at least one embodiment, platform controller hub 630 enables peripherals to connect to memory device 620 and processor 602 via a high-speed I/O bus. In at least one embodiment, I/O peripherals include, but are not limited to, an audio controller 646, a network controller 634, a firmware interface 628, a wireless transceiver 626, touch sensors 625, a data storage device 624 (e.g., hard disk drive, flash memory, etc.). In at least one embodiment, data storage device 624 can connect via a storage interface (e.g., SATA) or via a peripheral bus, such as a Peripheral Component Interconnect bus (e.g., PCI, PCI Express). In at least one embodiment, touch sensors 625 can include touch screen sensors, pressure sensors, or fingerprint sensors. In at least one embodiment, wireless transceiver 626 can be a Wi-Fi transceiver, a Bluetooth transceiver, or a mobile network transceiver such as a 3G, 4G, or Long Term Evolution (LTE) transceiver. In at least one embodiment, firmware interface 628 enables communication with system firmware, and can be, for example, a unified extensible firmware interface (UEFI). In at least one embodiment, network controller 634 can enable a network connection to a wired network. In at least one embodiment, a high-performance network controller (not shown) couples with interface bus 610. In at least one embodiment, audio controller 646 is a multi-channel high definition audio controller. In at least one embodiment, system 600 includes an optional legacy I/O controller 640 for coupling legacy (e.g., Personal System 2 (PS/2)) devices to system 600. In at least one embodiment, platform controller hub 630 can also connect to one or more Universal Serial Bus (USB) controllers 642 connect input devices, such as keyboard and mouse 643 combinations, a camera 644, or other USB input devices.

In at least one embodiment, an instance of memory controller 616 and platform controller hub 630 may be integrated into a discreet external graphics processor, such as external graphics processor 612. In at least one embodiment, platform controller hub 630 and/or memory controller 616 may be external to one or more processor(s) 602. For example, in at least one embodiment, system 600 can include an external memory controller 616 and platform controller hub 630, which may be configured as a memory controller hub and peripheral controller hub within a system chipset that is in communication with processor(s) 602.

In at least one embodiment, processing system 600 includes a compression component 115, which may execute on external graphics processor 612. Compression component 115 may be used to compress a region of an area of interest selected to be zoomed to accommodate the increased width and height of the zoomed area of interest. Details regarding compression component 115 are provided herein in conjunction with the preceding figures. In at least one embodiment, compression component 115 may be used in system 600 for maintaining neighboring contextual awareness with zoom as described herein.

Other variations are within spirit of present disclosure. Thus, while disclosed techniques are susceptible to various modifications and alternative constructions, certain illustrated embodiments thereof are shown in drawings and have been described above in detail. It should be understood, however, that there is no intention to limit disclosure to specific form or forms disclosed, but on contrary, intention is to cover all modifications, alternative constructions, and equivalents falling within spirit and scope of disclosure, as defined in appended claims.

Use of terms "a" and "an" and "the" and similar referents in context of describing disclosed embodiments (especially in context of following claims) are to be construed to cover both singular and plural, unless otherwise indicated herein or clearly contradicted by context, and not as a definition of a term. Terms "comprising," "having," "including," and "containing" are to be construed as open-ended terms (meaning "including, but not limited to,") unless otherwise noted. "Connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within range, unless otherwise indicated herein and each separate value is incorporated into specification as if it were individually recited herein. In at least one embodiment, use of term "set" (e.g., "a set of items") or "subset" unless otherwise noted or contradicted by context, is to be construed as a nonempty collection comprising one or more members. Further, unless otherwise noted or contradicted by context, term "subset" of a corresponding set does not necessarily denote a proper subset of corresponding set, but subset and corresponding set may be equal.

Conjunctive language, such as phrases of form "at least one of A, B, and C," or "at least one of A, B and C," unless specifically stated otherwise or otherwise clearly contradicted by context, is otherwise understood with context as used in general to present that an item, term, etc., may be either A or B or C, or any nonempty subset of set of A and B and C. For instance, in illustrative example of a set having three members, conjunctive phrases "at least one of A, B, and C" and "at least one of A, B and C" refer to any of following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, term "plurality" indicates a state of being plural (e.g., "a plurality of items" indicates multiple items). In at least one embodiment, number of items in a plurality is at least two, but can be more when so indicated either explicitly or by context. Further, unless stated otherwise or otherwise clear from context, phrase "based on" means "based at least in part on" and not "based solely on."

Operations of processes described herein can be performed in any suitable order unless otherwise indicated herein or otherwise clearly contradicted by context. In at least one embodiment, a process such as those processes described herein (or variations and/or combinations thereof) is performed under control of one or more computer systems configured with executable instructions and is implemented as code (e.g., executable instructions, one or more computer programs or one or more applications) executing collectively on one or more processors, by hardware or combinations thereof. In at least one embodiment, code is stored on a computer-readable storage medium, for example, in form of a computer program comprising a plurality of instructions executable by one or more processors. In at least one embodiment, a computer-readable storage medium is a non-transitory computer-readable storage medium that excludes transitory signals (e.g., a propagating transient electric or electromagnetic transmission) but includes non-transitory data storage circuitry (e.g., buffers, cache, and queues) within transceivers of transitory signals. In at least one embodiment, code (e.g., executable code or source code) is stored on a set of one or more non-transitory computer-readable storage media having stored thereon executable instructions (or other memory to store executable instructions) that, when executed (i.e., as a result of being executed) by one or more processors of a computer system, cause computer system to perform operations described herein. In at least one embodiment, set of non-transitory computer-readable storage media comprises multiple non-transitory computer-readable storage media and one or more of individual non-transitory storage media of multiple non-transitory computer-readable storage media lack all of code while multiple non-transitory computer-readable storage media collectively store all of code. In at least one embodiment, executable instructions are executed such that different instructions are executed by different processors—for example, a non-transitory computer-readable storage medium store instructions and a main central processing unit ("CPU") executes some of instructions while a graphics processing unit ("GPU") executes other instructions. In at least one embodiment, different components of a computer system have separate processors and different processors execute different subsets of instructions.

Accordingly, in at least one embodiment, computer systems are configured to implement one or more services that singly or collectively perform operations of processes described herein and such computer systems are configured with applicable hardware and/or software that enable performance of operations. Further, a computer system that implements at least one embodiment of present disclosure is a single device and, in another embodiment, is a distributed computer system comprising multiple devices that operate differently such that distributed computer system performs operations described herein and such that a single device does not perform all operations.

Use of any and all examples, or exemplary language (e.g., "such as") provided herein, is intended merely to better illuminate embodiments of disclosure and does not pose a limitation on scope of disclosure unless otherwise claimed. No language in specification should be construed as indicating any non-claimed element as essential to practice of disclosure.

All references, including publications, patent applications, and patents, cited herein are hereby incorporated by reference to same extent as if each reference were individually and specifically indicated to be incorporated by reference and were set forth in its entirety herein.

In description and claims, terms "coupled" and "connected," along with their derivatives, may be used. It should be understood that these terms may be not intended as synonyms for each other. Rather, in particular examples, "connected" or "coupled" may be used to indicate that two or more elements are in direct or indirect physical or electrical contact with each other. "Coupled" may also mean that two or more elements are not in direct contact with each other, but yet still co-operate or interact with each other.

Unless specifically stated otherwise, it may be appreciated that throughout specification terms such as "processing," "computing," "calculating," "determining," or like, refer to action and/or processes of a computer or computing system, or similar electronic computing device, that manipulate and/or transform data represented as physical, such as electronic, quantities within computing system's registers and/or memories into other data similarly represented as physical quantities within computing system's memories, registers or other such information storage, transmission or display devices.

In a similar manner, term "processor" may refer to any device or portion of a device that processes electronic data from registers and/or memory and transform that electronic data into other electronic data that may be stored in registers and/or memory. As non-limiting examples, "processor" may be a CPU or a GPU. A "computing platform" may comprise one or more processors. As used herein, "software" processes may include, for example, software and/or hardware entities that perform work over time, such as tasks, threads, and intelligent agents. Also, each process may refer to multiple processes, for carrying out instructions in sequence or in parallel, continuously or intermittently. In at least one embodiment, terms "system" and "method" are used herein interchangeably insofar as system may embody one or more methods and methods may be considered a system.

In present document, references may be made to obtaining, acquiring, receiving, or inputting analog or digital data into a subsystem, computer system, or computer-implemented machine. In at least one embodiment, process of obtaining, acquiring, receiving, or inputting analog and digital data can be accomplished in a variety of ways such as by receiving data as a parameter of a function call or a call to an application programming interface. In at least one embodiment, processes of obtaining, acquiring, receiving, or inputting analog or digital data can be accomplished by transferring data via a serial or parallel interface. In at least one embodiment, processes of obtaining, acquiring, receiving, or inputting analog or digital data can be accomplished by transferring data via a computer network from providing entity to acquiring entity. In at least one embodiment, references may also be made to providing, outputting, transmitting, sending, or presenting analog or digital data. In various examples, processes of providing, outputting, transmitting, sending, or presenting analog or digital data can be accomplished by transferring data as an input or output parameter of a function call, a parameter of an application programming interface or interprocess communication mechanism.

Although descriptions herein set forth example implementations of described techniques, other architectures may be used to implement described functionality, and are intended to be within scope of this disclosure. Furthermore, although specific distributions of responsibilities may be defined above for purposes of description, various functions and responsibilities might be distributed and divided in different ways, depending on circumstances.

Furthermore, although subject matter has been described in language specific to structural features and/or methodological acts, it is to be understood that subject matter claimed in appended claims is not necessarily limited to specific features or acts described. Rather, specific features and acts are disclosed as exemplary forms of implementing the claims.

What is claimed is:

1. A method comprising:

identifying an area of interest within a visual output of a surgical site;

performing a zoom operation on the area of interest to generate a magnified area of interest;

determining, based on an amount of zoom associated with the zoom operation, an occluded region around the area of interest within the visual output, wherein the occluded region is a region of the visual output generated based on a difference between the magnified area of interest and the area of interest within the visual output prior to performing the zoom operation;

applying a non-linear compression to the occluded region of the visual output to generate a compression zone within the magnified area of interest, wherein the compression zone has a magnification that varies based on radial distance, an inner portion of the compression zone having a first magnification based on a magnification of the magnified area of interest and an outer portion of the compression zone having a second magnification based on a magnification of a remainder of the visual output; and updating the magnified area of interest by replacing at least one pixel of the occluded region with at least one pixel of the compression zone.

2. The method of claim 1, wherein the visual output of the surgical site is an image.

3. The method of claim 1, wherein identifying the area of interest within the visual output of the surgical site includes cropping the area of interest from the visual output of the surgical site.

4. The method of claim 3, further comprising:

stitching the magnified area of interest comprising the compression zone to the visual output of the surgical site.

5. The method of claim 1, wherein the visual output of the surgical site is one frame of a video of the surgical site, and wherein the identifying, the performing, the determining, the applying, the updating are performed for a plurality of frames of the video.

6. The method of claim 5, wherein the video is a live feed of the surgical site, the method further comprising:

outputting the live feed of the video comprising the visual output and the magnified area of interest.

7. The method of claim 1, wherein applying non-linear compression to the occluded region comprises:

obtaining, based on the zoom operation, a scale factor;

determining a zoom area percentage based on a radius between a center of the magnified area of interest and a radius of the magnified area of interest;

determining, based on the zoom area percentage and the scale factor, a power coefficient;

for each pixel of the occluded region, determining, based on the power coefficient, a new pixel value for the respective pixel; and updating the respective pixel with the new pixel value.

8. The method of claim 7, wherein determining the new pixel value includes obtaining polar coordinates of the respective pixel, determining a new radius value by applying the power coefficient to a radius value of the polar coordinates of the respective pixel, and obtaining, based on the new radius value, cartesian coordinates of the new pixel.

9. A system comprising:

an image capture device configured to acquire at least one frame of a surgical site; and one or more processors, operatively coupled to the image capture device, the one or more processors to perform operations comprising:

identifying, based on the at least one frame of the surgical site, an area of interest within a visual output of the surgical site;

performing a zoom operation on the area of interest to generate a magnified area of interest;

determining, based on an amount of zoom associated with the zoom operation, an occluded region around the area of interest within the visual output, wherein the occluded region is a region of the visual output generated based on a difference between the magnified area of interest and the area of interest within the visual output prior to performing the zoom operation;

applying a non-linear compression to the occluded region of the visual output to generate a compression zone within the magnified area of interest, wherein the compression zone has a magnification that varies based on radial distance, an inner portion of the compression zone having a first magnification based on a magnification of the magnified area of interest and an outer portion of the compression zone having a second magnification based on a magnification of a remainder of the visual output; and updating the magnified area of interest by replacing at least one pixel of the occluded region with at least one pixel of the compression zone.

10. The system of claim 9, wherein the visual output of the surgical site is an image.

11. The system of claim 9, wherein identifying the area of interest within the visual output of the surgical site includes cropping the area of interest from the visual output of the surgical site.

12. The system of claim 11, wherein the one or more processors is to perform further operations comprising:

stitching the magnified area of interest comprising the compression zone to the visual output of the surgical site.

13. The system of claim 9, wherein the at least one frame associated with the visual output of the surgical site is a frame of a video of the surgical site, and wherein the identifying, the performing, the determining, the applying, the updating are performed for a plurality of frames of the video.

14. The system of claim 13, wherein the video is a live feed of the surgical site, the one or more processors to perform operations further comprising:

outputting the live feed of the video comprising the visual output and the magnified area of interest.

15. The system of claim 9, wherein applying non-linear compression to the occluded region comprises:

obtaining, based on the zoom operation, a scale factor;

determining a zoom area percentage based on a radius between a center of the magnified area of interest and a radius of the magnified area of interest;

determining, based on the zoom area percentage and the scale factor, a power coefficient;

for each pixel of the occluded region, determining, based on the power coefficient, a new pixel value for the respective pixel; and updating the respective pixel with the new pixel value.

16. The system of claim 15, wherein determining the new pixel value includes obtaining polar coordinates of the respective pixel, determining a new radius value by applying the power coefficient to a radius value of the polar coordinates of the respective pixel, and obtaining, based on the new radius value, cartesian coordinates of the new pixel.

17. A non-transitory computer-readable storage medium comprising instructions that, when executed by a processing device, cause the processing device to perform operations comprising:

identifying an area of interest within a visual output of a surgical site;

performing a zoom operation on the area of interest to generate a magnified area of interest;

determining, based on an amount of zoom associated with the zoom operation, an occluded region around the area of interest within the visual output, wherein the occluded region is a region of the visual output generated based on a difference between the magnified area of interest and the area of interest within the visual output prior to performing the zoom operation;

applying a non-linear compression to the occluded region of the visual output to generate a compression zone within the magnified area of interest, wherein the compression zone has a magnification that varies based on radial distance, an inner portion of the compression zone having a first magnification based on a magnification of the magnified area of interest and an outer portion of the compression zone having a second magnification based on a magnification of a remainder of the visual output; and updating the magnified area of interest by replacing at least one pixel of the occluded region with at least one pixel of the compression zone.

18. The non-transitory computer-readable storage medium of claim 17, wherein applying non-linear compression to the occluded region comprises:

obtaining, based on the zoom operation, a scale factor;

determining a zoom area percentage based on a radius between a center of the magnified area of interest and a radius of the magnified area of interest;

determining, based on the zoom area percentage and the scale factor, a power coefficient;

for each pixel of the occluded region, determining, based on the power coefficient, a new pixel value for the respective pixel; and updating the respective pixel with the new pixel value.

19. The non-transitory computer-readable storage medium of claim 17, wherein identifying the area of interest within the visual output of a surgical site includes cropping the area of interest from the visual output of the surgical site.

20. The non-transitory computer-readable storage medium of claim 17, wherein the visual output of the surgical site is one frame of a video of the surgical site, and wherein the identifying, the performing, the determining, the applying, the updating are performed for a plurality of frames of the video.

* * * * *